United States Patent
Kusunose et al.

(10) Patent No.: US 7,850,852 B2
(45) Date of Patent: Dec. 14, 2010

(54) PROCESS FOR PRODUCING AMINO ACID OR SALT THEREOF BY COLUMN TECHNIQUE AND PRODUCTION APPARATUS THEREOF

(75) Inventors: Yasuhiro Kusunose, Kawasaki (JP); Kenji Takahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 774 days.

(21) Appl. No.: 11/844,904

(22) Filed: Aug. 24, 2007

(65) Prior Publication Data
US 2008/0039647 A1 Feb. 14, 2008

Related U.S. Application Data

(60) Division of application No. 11/166,755, filed on Jun. 27, 2005, now Pat. No. 7,311,836, which is a continuation of application No. PCT/JP03/16636, filed on Dec. 24, 2003.

(30) Foreign Application Priority Data
Dec. 27, 2002 (JP) .............................. 2002-381470

(51) Int. Cl.
*B01D 15/08* (2006.01)
(52) U.S. Cl. .................. 210/635; 210/638; 210/656; 210/670; 210/677; 435/106; 435/107; 435/108; 435/113; 435/116
(58) Field of Classification Search ................. 210/635, 210/638, 656, 670, 677, 180; 435/106, 107, 435/108, 113, 116
See application file for complete search history.

(56) References Cited

U.S. PATENT DOCUMENTS
4,256,471 A 3/1981 Goorden
5,017,480 A * 5/1991 Mori et al. ................. 435/106

(Continued)

FOREIGN PATENT DOCUMENTS
EP 0018 028 10/1980

(Continued)

OTHER PUBLICATIONS

A. Zammouri, et al., "Ion-Exchange Equilibria of Amino Acids on Strong Anionic Resins", Ind. Eng. Chem. Res., vol. 39, 2000, pp. 1397-1408.

(Continued)

*Primary Examiner*—Ernest G Therkorn
(74) *Attorney, Agent, or Firm*—Oblon, Spivak, McClelland, Maier & Neustadt, L.L.P.

(57) ABSTRACT

According to the process for producing amino acid or salt thereof in the present invention, in the adsorption step, an amino acid-containing aqueous solution is fed into a pressure tight column so that a free amino acid is adsorbed on a carbonate-type anion exchange resin packed in the pressure tight column. Subsequently, in the elution step, eluent liquid containing a hydrogen carbonate ion and/or a carbonate ion is injected into the pressure tight column in a pressurized state to elute the amino acid adsorbed on the anion exchange resin and simultaneously to regenarate the anion exchange resin into the carbonate-type. In the case of purifying an acidic amino acid, an aqueous ammonium carbonate solution is employed as the eluent liquid. In the case of purifying a neutral amino acid, an aqueous carbonic acid solution, an aqueous hydrogen carbonate solution, an aqueous ammonium hydrogen carbonate solution or an aqueous ammonium carbonate solution is employed as the eluent liquid. Further, a breakthrough liquid discharged from the adsorption step is optionally concentrated to remove the volatile carbonate acid component and ammonium component from the breakthrough liquid. Thus, the solid content in the breakthrough liquid can be reduced.

1 Claim, 3 Drawing Sheets

U.S. PATENT DOCUMENTS 5,071,560 A * 12/1991 McCulloch et al. .......... 210/635
6,001,255 A * 12/1999 Eyal et al. .................. 210/638

FOREIGN PATENT DOCUMENTS

GB  628748  9/1946
JP  55-139815  11/1980

OTHER PUBLICATIONS

A. zammouri, et al., "Displacement Chromatography of Amino Acids by Carbon Dioxide Dissolved in Water", Ind. Eng. Chem. Res., vol. 38, 1999, pp. 4860-4867.

Z. Pasztor, et al., "Elution of Amino Acids from Anion Exchange Columns by Means of an Aqueous Solution of Carbon Dioxide Under Pressure", AICHe Annual Meeting, Miami, Nov. 15-20, 1998.

A. Zammouri, et al., "Displacement Chromatography of Amino Acids On A Strong Base Resin by Means of an Aqueous Solution of Carbon Dioxide Under Pressure", Recents Progres en Geni des Procedes, vol. 13, No. 68, 1999, pp. 213-220.

Z. Pasztor, et al., "Elution Chromatography and Displacement Chromatography of Amino Acids On A Strong Base Resin by Means of an Aqueous Solution of Carbon Dioxide Under Pressure", Ion Exchange at the Millennium, Proceedings of IEX 2000, 8th, Cambridge, Jul. 16-21, 2000, pp. 289-297.

* cited by examiner

PROCESS FOR PRODUCING AMINO ACID OR SALT THEREOF BY COLUMN TECHNIQUE AND PRODUCTION APPARATUS THEREOF

This application is a Divisional of U.S. application Ser. No. 11/166,755, filed on Jun. 27, 2005, now U.S. Pat. No. 7,311,836, which is a continuation of PCT/JP03/16636, filed on Dec. 24, 2003.

TECHNICAL FIELD

The present invention relates to a process for producing an amino acid or an amino acid salt from an amino acid-containing aqueous solution using a carbonate-type anion exchange resin, and a system of reducing the amount of by-products generated from an adsorption step and an elution step and recovering an eluent from a breakthrough liquid and an eluate for recycling.

BACKGROUND ART

In the process of isolating and purifying an amino acid from an amino acid-containing aqueous solution, a purification method using an ion exchange resin is one of the most classical and representative unit operating methods. Since amino acids are amphoteric electrolytes, it is possible to use any of a cation exchange resin and an anion exchange resin for the purification thereof. In general, a strongly acidic cation exchange resin is most frequently employed. In this case, it is a general method that a fermentation liquid controlled to an appropriate hydrogen ion concentration is passed though a resin column and an adsorbed amino acid is eluted and recovered with an ammonium aqueous solution. A representative example is purification of L-lysine, which is one of amino acids for feedstuff, with a cation exchange resin. The ion exchange resin process has merits that the energy cost is smaller than a crystallization process or an electrodialysis process, and the facility cost is small in comparison with a membrane separation process.

The ion exchange resin process is roughly separated into an adsorption step and an elution step. The adsorption step is an adsorption step of adsorbing an amino acid (AA) on a resin (Resin) (the following formula (1)) and the elution step is a step of eluting the amino acid adsorbed on the resin using a predetermined eluent liquid (E) (the following formula (2)).

Resin-E+AA→Resin-AA+E    (1)

Resin-AA+E→Resin-E+AA    (2)

In such an ion exchange resin-treating operation, a liquid which is discharged from the adsorption step and contains substances not adsorbed on the ion exchange resin is called a breakthrough liquid, and a liquid which is discharged from the elution step and contains the amino acid is called an eluate. The problems of the ion exchange resin process are as follows. First, since the eluate contains not only the amino acid which is an objective substance but also the eluent, it is necessary to separate them. Since the ion exchange reaction is an equilibrium reaction, an excessive eluent relative to the amount of the amino acid in terms of mol ratio is necessarily required to elute the amino acid from the ion exchange resin. It can be represented by the following formula (3).

Resin-AA+nE→Resin-E+AA+(n−1)E    (3)

(wherein n>1)

Therefore, since the excess eluent ((n−1)E in the formula (3)) is mixed into the eluate, it is necessary to separate the amino acid from the eluent after the elution step. When the eluent is a volatile substance such as an ammonium component, it is easy to remove the excessive eluent by conducting mere concentration. However, in the case of a nonvolatile salt or the like, it is difficult to separate the salt and thereby the whole process becomes complex and the increase in a production cost is unavoidable.

The second problem relates to the separation of the eluent which is also present in the breakthrough liquid. Into the breakthrough liquid, not only non-adsorbed substances in the amino acid-containing aqueous solution, but also the eluent is eluted from the ion exchange resin by adsorbing the amino acid on the ion exchange resin, as shown by E in the right side of the formula (1). This eluent is usually converted into a by-product by forming a salt with a non-adsorbed substance in the fermentation liquid or the like. For example, when a lysine fermentation liquid is purified with a cation exchange resin using an ammonium component as an eluent, the sulfate ion in the fermentation liquid and the ammonium component in the eluent are combined to form ammonium sulfate.

There may be no problem when such a by-product is a volatile substance or the like and is easily recovered. However, since the by-product is usually a stable salt, it still remains until the end of the process. Therefore, in the process for purifying a fermentation liquid using the ion exchange process, generation of a commensurate by-product is unavoidable.

As one method for overcoming the defect of such an ion exchange resin process, there has been known a method of ion-exchanging an amino acid adsorbed with an anion exchange resin using as an eluent liquid, an aqueous carbonic acid solution obtained by dissolving carbon dioxide gas in water under predetermined pressure (Pasztor, Zs.; Chanel, S.; Grevillot, G. Elution of amino acids from anion exchange columns by means of an aqueous solution of carbon dioxide under pressure. AIChE Annual Meeting, Miami, Nov. 15-19, 1998). In this method, when the obtained eluate is released to normal pressure, the eluent present in the eluate, i.e., a carbonate ion is converted into gas to vaporize, and hence the eluent does not remain in the eluate as shown in formula (4). Therefore, it becomes unnecessary to separate the eluent from the objective substance after the elution step, and thus the purification of the eluate is simplified.

Resin-AA⁻+nHCO₃⁻→Resin-HCO₃⁻+ AA⁻+(n−1)OH⁻+(n−1)CO₂↑    (4)

(wherein n>1)

There are three problems in this method. First, in the adsorption step of re-adsorbing an amino acid on a carbonate-type anion exchange resin after the elution of the amino acid, carbon dioxide gas foams as shown in formulae (5) and (6).

Resin-HCO₃⁻+AA⁻→Resin-AA⁻+nHCO₃⁻    (5)

HCO₃⁻→OH⁻+CO₂↑    (6)

When the carbon dioxide gas is generated in the column, smooth ion exchange is not achieved since channeling of the liquid occurs. Second, in order to re-adsorb the amino acid on the anion exchange resin, it is necessary to regenerate the carbonate-type anion exchange resin to the OH-type anion exchange resin once, and hence the process becomes complex. Industrially, it is preferable to adsorb the amino acid directly on the carbonate-type anion exchange resin. Third, in the elution step, amino acids capable of being eluted are limited to neutral amino acids. The elution reaction is conducted at around the neutral hydrogen ion concentration. For example, when the amino acid is an acidic amino acid, since the acidic amino acid is in the form of an anion, the amino acid once eluted from the resin is immediately re-adsorbed on the resin. Usual ion exchange reaction proceeds microscopically with repeating the elution and re-adsorption. However, when an aqueous carbonic acid solution wherein carbon dioxide gas is dissolved in water is used as an eluent liquid, the carbonate ion concentration in the eluent liquid is low and the carbonate ion necessary for re-elution of the re-adsorbed amino acid is not necessarily sufficient. As a result, a sufficient elution cannot be achieved in the case of an acidic amino acid.

On the other hand, with regard to the recovery of eluents such as ammonium radical and carbonate radical, JP-A-55-139815 discloses a method of obtaining carbon dioxide in a remaining liquid phase as gaseous carbon dioxide after fractional distillation of an ammonium component contained in an aqueous solution.

DISCLOSURE OF THE INVENTION

The present invention relates to a process for producing an amino acid or a salt thereof, which comprises:

an adsorption step comprising adsorbing a free amino acid contained in an amino acid-containing aqueous solution while the amino acid-containing aqueous solution passes through a pressure tight column packed with a carbonate-type anion exchange resin under elevated pressure, and an elution step comprising injecting an eluent liquid containing a hydrogen carbonate ion and/or a carbonate ion under pressure into the pressure tight column under elevated pressure to elute the amino acid adsorbed on the anion exchange resin, and simultaneously to regenerate the anion exchange resin into the carbonate-type, to thereby obtain the amino acid or the salt thereof.

The second of the present invention is the process for producing an amino acid or a salt thereof according to the first of the present invention, wherein the amino acid contained in the amino acid-containing aqueous solution is an acidic amino acid, a neutral amino acid, or a basic amino acid.

The third of the present invention is the process for producing an amino acid or a salt thereof according to the first or the second of the present invention, wherein the neutral amino acid is cystine, phenylalanine, threonine, tyrosine, serine, tryptophan, citrulline, isoleucine, leucine, valine, alanine, proline, glutamine, methionine, or glycine; the acidic amino acid is glutamic acid or aspartic acid; and the basic amino acid is lysine, ornithine, arginine, or histidine.

The fourth of the present invention is the process for producing an amino acid or a salt thereof according to any one of the first to third of the present invention, wherein the elevated pressure is at least 0.1 Mpa.

The fifth of the present invention is the process for producing an amino acid or a salt thereof according to any one of the first to fourth of the present invention, wherein the eluent liquid is an aqueous carbonic acid and hydrogen carbonate solution, an aqueous ammonium carbonate solution or an aqueous ammonium hydrogen carbonate solution for the neutral amino acid; an aqueous ammonium carbonate solution or an aqueous ammonium hydrogen carbonate solution for the acidic amino acid; and an aqueous ammonium carbonate solution or an aqueous ammonium hydrogen carbonate solution for the basic amino acid.

The sixth of the present invention is an apparatus for producing an amino acid or a salt thereof, which conducts an adsorption step of adsorbing the amino acid in an amino acid-containing aqueous solution on an anion exchange resin and an elution step of eluting said adsorbed amino acid from the anion exchange resin, said apparatus comprising at least a pressure tight column (A), a reservoir tank (B), and a transfer pipe (C) connecting therewith, wherein the pressure tight column (A) comprises a valve which controls a discharge of a breakthrough liquid, an eluent liquid, or the like and is disposed in the vicinity of a bottom outlet, and a valve which controls an inner pressure at the upper portion thereof, the reservoir tank (B) comprises a line comprising a pressurizing equipment by means of air and/or an inert gas and carbon dioxide gas and a valve which feeds and controls the amino acid-containing aqueous solution, an eluent liquid or water and an eluent, reserves a gas or a liquid, and comprises a valve which controls a discharge amount and is disposed in the vicinity of a bottom outlet, and the transfer line (C) optionally comprises a pump for liquid transfer.

The seventh of the present invention is the apparatus for producing an amino acid or a salt thereof according to the sixth of the present invention, wherein the amino acid contained in the amino acid-containing aqueous solution is an acidic amino acid, a neutral amino acid, or a basic amino acid.

The eighth of the present invention is the apparatus for producing an amino acid or a salt thereof according to the sixth or seventh of the present invention, wherein the neutral amino acid is cystine, phenylalanine, threonine, tyrosine, serine, tryptophan, citrulline, isoleucine, leucine, valine, alanine, proline, glutamine, methionine, or glycine; the acidic amino acid is glutamic acid or aspartic acid; and the basic amino acid is lysine, ornithine, arginine, or histidine.

The ninth of the present invention is the apparatus for producing an amino acid or a salt thereof according to any one of the sixth to eighth of the present invention, wherein the eluent liquid is an aqueous carbonic acid and hydrogen carbonate solution, an aqueous ammonium carbonate solution, or an aqueous ammonium hydrogen carbonate solution for the neutral amino acid; an aqueous ammonium carbonate solution or an aqueous ammonium hydrogen carbonate solution for the acidic amino acid; and an aqueous ammonium carbonate solution or an aqueous ammonium hydrogen carbonate solution for the basic amino acid.

The tenth of the present invention is a process for producing sodium acidic amino acid or potassium acidic amino acid from an acidic amino acid-containing aqueous solution, which comprises:

removing a carbon dioxide component, a carbonate ion, and an ammonium component excessive in an acidic amino acid ammonium salt-containing eluate according to any one of the first to fifth of the present invention under normal pressure by optionally heating, adding a sodium hydroxide or a potassium hydroxide in an amount almost equimolar to the acidic amino acid to obtain an aqueous sodium acidic amino acid solution or an aqueous potassium acidic amino acid solution, and removing the water solvent.

The eleventh of the present invention is a process for producing a basic amino acid salt from a basic amino acid-containing aqueous solution, which comprises:

removing a carbon dioxide component, a carbonate ion, and an ammonium component excessive in a basic amino acid-containing eluate according to any one of the first to fifth of the present invention by optionally heating or reducing pressure, adding an hydrochloric acid in an amount almost equimolar to the basic amino acid, and removing a water solvent of the resulting aqueous basic amino acid hydrochloride solution.

The twelfth of the present invention is a method for recovering an eluent, which comprises heating or optionally heating under reduced pressure, a breakthrough liquid which is discharged from a pressure tight column through an adsorption step of adsorbing a free amino acid contained in an amino acid-containing aqueous solution on the pressure tight column while the solution passes through the pressure tight column packed with a carbonate-type anion exchange column under elevated pressure, and/or an eluate which is discharged from the pressure tight column through an elution step comprising injecting an eluent liquid containing a hydrogen carbonate ion and/or a carbonate ion under pressure into the pressure tight column under elevated pressure, eluting the amino acid adsorbed on the anion exchange resin, and simultaneously regenerating the anion exchange resin into the carbonate-type and from which the amino acid or a salt thereof is removed, to vaporize a carbonate ion, an acidic carbonate ion, or an ammonium ion to thereby recover the eluent as a carbon dioxide gas or an ammonia gas.

DESCRIPTION OF REFERENCE NUMERALS AND SIGNS (A), a pressure tight column
(B), b reservoir tank
(C) transfer line
c valve
d air line
e valve
f valve
g pump
h valve
i carbon dioxide gas line
j cooling water line
k cooling water line
l cooling water line
m cooling water line
n valve
o fermentation liquid, water, aqueous ammonium solution feed inlet
p valve
q liquid drainage line
r valve
s breakthrough liquid, washing waste liquid, eluate drainage line
t pump
u valve
v1, v2 steam line
w1, w2 compressor
x ammonia gas line
y carbon dioxide gas line
z breakthrough liquid, washing waste liquid, eluate drainage line
da deaerating tank
sp separation apparatus

BEST MODE FOR CARRYING OUT THE INVENTION

The present invention includes an adsorption step of the various kinds of amino acids on a carbonate-type anion exchange resin, an elution step of adsorbed amino acids with an eluent liquid, and simultaneous regeneration of the anion exchange resin to the carbonate-type. Furthermore, it includes an elution step of obtaining an eluate containing the amino acids and a production step of obtaining the amino acids or salts thereof by subjecting the eluate to concentration, purification, and the like.

In the adsorption step, an amino acid-containing aqueous solution whose hydrogen ion concentration is optionally controlled is fed to a pressure tight column, and, while the solution passes through the pressure tight column, the free amino acids contained therein are adsorbed on the carbonate-type anion exchange resin packed in the pressure tight column. Then, in the elution step, an eluent liquid containing a hydrogen carbonate ion and/or a carbonate ion is injected into the pressure tight column in a pressurized state, the amino acids adsorbed on the anion exchange resin are eluted, and simultaneously the anion exchange resin is regenerated into the carbonate-type. The following will describe the characteristics of the invention on every step in further detail.

Adsorption Step

The adsorption step is carried out in a pressure tight column under pressure. For maintaining the pressurized state, when the pressure tight column is fitted with a pressurizing apparatus which is capable of direct pressurization with a gas, the pressure tight column is pressurized to a pressure of 0.1 MPa or higher using a gas which is almost insoluble in water, such as air, helium, nitrogen, or argon. Moreover, it may be pressurized directly to 0.1 MPa or higher by utilizing water pressure of a reservoir tank without using the pressurizing apparatus with a gas. Necessary water pressure can be maintained by placing the reservoir tank at an elevated place or pressurizing the reservoir tank with a gas.

Then, the amino acid-containing aqueous solution is fed to adsorb a free amino acid on the anion exchange resin. At this time, a carbonate ion is eluted from the anion exchange resin into a feed liquid, but carbon dioxide gas does not foam since the inside of the pressure tight column is pressurized. Therefore, the channeling of the liquid caused by bubbles in the anion exchange resin column, which is induced at normal pressure, does not occur and the ion exchange reaction smoothly proceeds. It is necessary to set the hydrogen ion concentration of the feed liquid should at the range where the ionic form of the amino acid is anion. At this time, as a hydrogen ion concentration controlling liquid to be used, ammonia, which is easily recovered from the breakthrough liquid, is employed as mentioned below.

The control of the hydrogen ion concentration varies depending on the kinds of the amino acids, i.e., acidic, neutral, or basic ones. In the case of an acidic amino acid, since the acidic amino acid itself is charged negatively even when an aqueous solution thereof is neutral, i.e., at around pH 7, the acidic amino acid can be adsorbed on the anion exchange resin without controlling the hydrogen ion concentration. The hydrogen ion concentration may be further controlled with an ammonium component, if necessary. In the case of a neutral amino acid, when an aqueous solution thereof is in the state of pH 7, the neutral amino acid is not charged negatively. Therefore, the neutral amino acid cannot be adsorbed on the anion exchange resin as it is. Thus, an alkali is added in order to charge the neutral amino acid negatively. As the alkali, an aqueous solution, such as an aqueous sodium hydroxide solution, an aqueous potassium hydroxide solution, or an aqueous ammonium solution can be used, but it is preferable to use an aqueous ammonium solution or liquid ammonia in view of the reduction of the by-products salts in the breakthrough liquid and the recovery and the recycle of the eluent, which are purposes of the present invention. In the case of a basic amino acid, when an aqueous solution thereof is in the state of pH 7, the basic amino acid is not charged negatively. Thus, an alkali is added until the hydrogen ion concentration reaches to a point where the amino acid is charged negatively, as in the case of the neutral amino acid. As the alkali, it is preferable to use an aqueous ammonium solution or liquid ammonia.

As the amino acid-containing aqueous solution to be used in the present invention, not only a pre-purified aqueous solution containing no solidifying salt but also an amino acid fermentation liquid in an unpurified state can be treated similarly. An aqueous solution which is obtained by subjecting a fermentation liquid to predetermined pre-treatments such as bacteria elimination, decoloration, and control of hydrogen ion concentration and an amino acid fermentation liquid itself which is obtained by aerobic fermentation of a predetermined producing bacteria using sugar source such as molasses or corn starch, nutrient, and inorganic matter as fermentation materials are also included. In this case, for carrying out the present invention, it is preferable to subject the liquid to a predetermined pre-treatment such as removal of bacteria body by membrane separation, centrifuge, or the like or decoloration.

The pressure tight column to be used in the present invention is a pressure tight column packed with an anion exchange resin, which is made of glass or stainless steel, has a withstanding pressure of at least 0.1 MPa, and is preferably fitted with a temperature controlling apparatus such as a jacket in order to be able to control the temperature of a process liquid. The pressure tight column may possess a pressurizing apparatus with a gas almost insoluble in water, such as air, helium, nitrogen, or argon, in order to maintain the pressurized state.

Among various amino acids, the neutral amino acid is cystine, phenylalanine, threonine, tyrosine, serine, tryptophan, citrulline, isoleucine, leucine, valine, alanine, proline, glutamine, methionine, glycine, or the like, the acidic amino acid is glutamic acid, aspartic acid, or the like, and the basic amino acid is lysine, arginine, ornithine, histidine, or the like. These amino acids may be any of L-form, D-form, and racemic form.

Elution Step

The following will describe an elution step of eluting an amino acid from an amino acid-adsorbed resin. In the case of an aqueous carbonic acid solution, the preparation of the eluent liquid is carried out by injecting a carbon dioxide gas into a reservoir tank filled with water and applying predetermined pressure. In the case that the eluent liquid is an aqueous ammonium carbonate solution, it is carried out by injecting carbon dioxide gas and ammonia gas into a reservoir tank filled with water and applying predetermined pressure, or by injecting carbon dioxide gas into an aqueous ammonium solution and applying predetermined pressure. Specifically, the eluent liquid is obtained by feeding water or an aqueous ammonium solution into a reservoir tank and then carbon dioxide gas is injected thereinto to achieve a stationary state, while the pressure of the reservoir tank at the stationary state is 0.1 MPa or higher. In order to achieve a homogeneous concentration in the reservoir tank quickly, it is preferable for the reservoir tank to possess a stirrer or a self-circulating pump. The temperature is preferably a low temperature in order to increase the solubility of carbon dioxide gas, but attention should be paid in the case of an amino acid having a low solubility. The chemical reactions in these cases are as shown in formulae (7) to (10).

In the case of dissolving carbon dioxide gas into water $$H_2O + CO_2(gas) \rightarrow H^+ + HCO_3^- \qquad (7)$$

$$H_2O + CO_2(gas) \rightarrow 2H^+ + CO_3^{2-} \qquad (8)$$

In the case of dissolving carbon dioxide gas into an aqueous ammonium solution $$2NH_4OH + CO_2(gas) \rightarrow 2NH_4^+ + CO_3^{2-} + H_2O \qquad (9)$$

$$NH_4OH + CO_2(gas) \rightarrow NH_4^+ + HCO_3^{2-} \qquad (10)$$

The aqueous carbonic acid solution or the aqueous ammonium carbonate solution thus prepared under pressure is fed to a pressure tight column. In this case, an aqueous carbonic acid solution, an aqueous hydrogen carbonate solution, an aqueous ammonium carbonate solution, or an aqueous ammonium hydrogen carbonate solution is used for the neutral amino acid, an aqueous ammonium carbonate solution or an aqueous ammonium hydrogen carbonate solution is used for the acidic amino acid, and an aqueous ammonium carbonate solution or an aqueous ammonium hydrogen carbonate solution is used for the basic amino acid. By using these aqueous carbonic acid solution, aqueous hydrogen carbonate solution, aqueous ammonium carbonate solution, or aqueous ammonium hydrogen carbonate solution, the amino acids adsorbed on the anion exchange resin are eluted from the anion exchange resin. At that time, the pressure of the pressure tight column is made 0.1 MPa or higher using carbon dioxide gas, but preferably, the pressure is higher than that in the reservoir tank for storing an eluate even when the pressure difference is small, in order to inhibit the bubble formation of the carbon dioxide gas in the pressure tight column. The ions contributing the ion exchange are anions such as carbonate ion ($CO_3^{2-}$) and hydrogen carbonate ion ($HCO_3^-$) generated according to the formulae (7) to (10). The ion exchange reactions in these cases expressed by chemical formulae are as follows.

In the case that the eluent liquid is an aqueous hydrogen carbonate solution, $$Resin\text{-}AAN^- + H^+ + HCO_3^- \rightarrow Resin\text{-}HCO_3^- AAN\text{-}H \qquad (11)$$

(wherein AAN is a neutral amino acid residue and AAN-H is a free neutral amino acid).

In the case that the eluent liquid is an aqueous carbonate solution, $$2Resin\text{-}AAN^- + 2H^+ + CO_3^{2-} \rightarrow Resin_2\text{-}CO_3^{2-} + 2AAN\text{-}H \qquad (12)$$

(wherein AAN is a neutral amino acid residue and AAN-H is a free neutral amino acid).

In the case that the eluent liquid is an aqueous ammonium hydrogen carbonate solution, $$\text{Resin-AAA}^- + \text{NH}_4^+ + \text{HCO}_3^- \rightarrow \text{Resin-HCO}_3^- + \text{AAA-NH}_4 \quad (13)$$

(wherein AAA is an acidic amino acid residue and AAA-NH$_4$ is an acidic amino acid ammonium salt)

In the case that the eluent liquid is an aqueous ammonium carbonate solution, $$2\text{Resin-AAA}^- + 2\text{NH}_4^+ + \text{CO}_3^{2-} \rightarrow \text{Resin}_2\text{-CO}_3^{2-} + 2\text{AAA-NH}_4 \quad (14)$$

(wherein AAA is an acidic amino acid residue and AAA-NH$_4$ is an acidic amino acid ammonium salt), $$\text{Resin-AAN}^- + \text{NH}_4^+ + \text{HCO}_3^- \rightarrow \text{Resin-HCO}_3^- + \text{AAA-NH}_4 \quad (15)$$

(wherein AAN is a neutral amino acid residue and AAA-NH$_4$ is a neutral amino acid ammonium salt), $$2\text{Resin-AAN}^- + 2\text{NH}_4^+ + \text{CO}_3^{2-} \rightarrow \text{Resin}_2\text{-CO}_3^{2-} + 2\text{AAA-NH}_4 \quad (16)$$

(wherein AAN is a neutral amino acid residue and AAA-NH$_4$ is a neutral amino acid ammonium salt), $$\text{Resin-AAB}^- + \text{NH}_4^+ + 2\text{HCO}_3^- \rightarrow \text{Resin-HCO}_3^- + \text{AAB-HCO}_3 + \text{NH}_4^+ \quad (17)$$

(wherein AAB is a basic amino acid residue and AAB-HCO$_3$ is a basic amino acid hydrogen carbonate salt), $$2\text{Resin-AAB}^- + 2\text{NH}_4^+ + 2\text{CO}_3^{2-} \rightarrow \text{Resin}_2\text{-CO}_3^{2-} + 2\text{AAB}_2\text{-CO}_3 + 2\text{NH}_4^+ \quad (18)$$

(wherein AAB is a basic amino acid residue and AAB$_2$-CO$_3$ is a basic amino acid carbonate salt).

In this case, the ionic form of the amino acid at the elution is a mixture of ± and +. The basic amino acid (monovalent) carbonate salt is a mixture of AAB-H and AAB-HCO$_3$.

On the anion exchange resin, as shown in the above formulae (11) to (18), a carbonate ion or a hydrogen carbonate ion contained in the eluent liquid is adsorbed instead of the amino acid after the amino acid is liberated. Therefore, the regenerated carbonate-type anion exchange resins can be recycled as a resin for the next adsorption step without further treatment.

When an aqueous carbonic acid solution or an aqueous hydrogen carbonate solution is used as the eluent, the resulting amino acid in the eluate is in a free form as shown in formulae (11) and (12), but when an aqueous ammonium carbonate solution is used as the eluent, an ammonium salt or a carbonate salt of the amino acid is obtained as shown in formulae (13), (14), (15), (16), (17), and (18). Since a product amino acid is usually distributed in a free form, it is preferable to use the aqueous carbonic acid solution as the eluent liquid. However, when the aqueous ammonium carbonate solution is used as the eluent liquid, the elution efficiency is high owing to a large amount of carbonate ion in the eluent liquid.

In the case of an acidic amino acid which is difficult to elute with the aqueous carbonic acid solution, it is preferable to use the aqueous ammonium carbonate solution as the eluent liquid. For the purification of a neutral amino acid, an aqueous carbonic acid solution, an aqueous hydrogen carbonate solution, an aqueous ammonium hydrogen carbonate solution, or an aqueous ammonium carbonate solution is used, and an aqueous ammonium carbonate solution or an aqueous ammonium hydrogen carbonate solution is used for the purification of a basic amino acid.

When a large amount of the amino acid-containing aqueous solution is treated within a short period of time, by sequentially carrying out a plurality of these steps simultaneously and in parallel, the adsorption step and the elution step can be carried out efficiently. Further, the amino acid can be produced similarly by using a batch which is capable of being pressurized, instead of using the pressure tight column.

Figure 3:
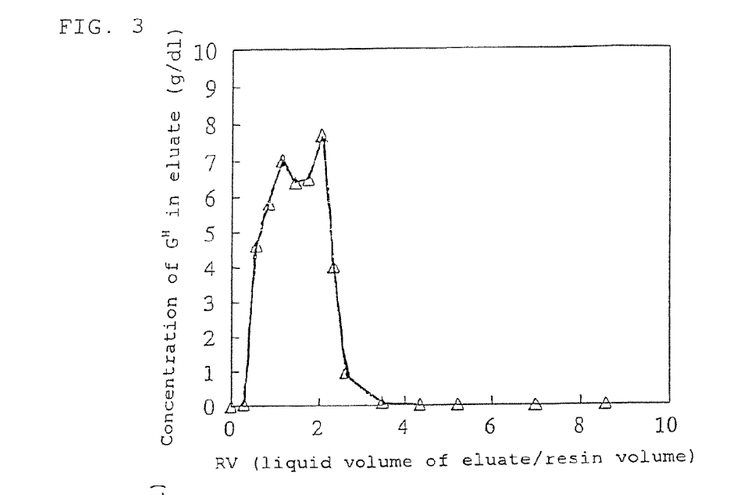
FIG. 3 shows an elution curve of an acidic amino acid from a carbonate-type anion exchange resin.
Figure 4:
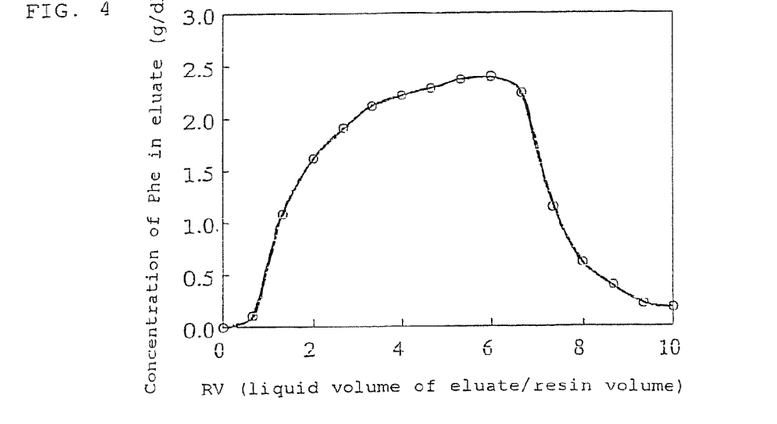
FIG. 4 shows an elution curve of a neutral amino acid from a carbonate-type anion exchange resin.
Figure 5:
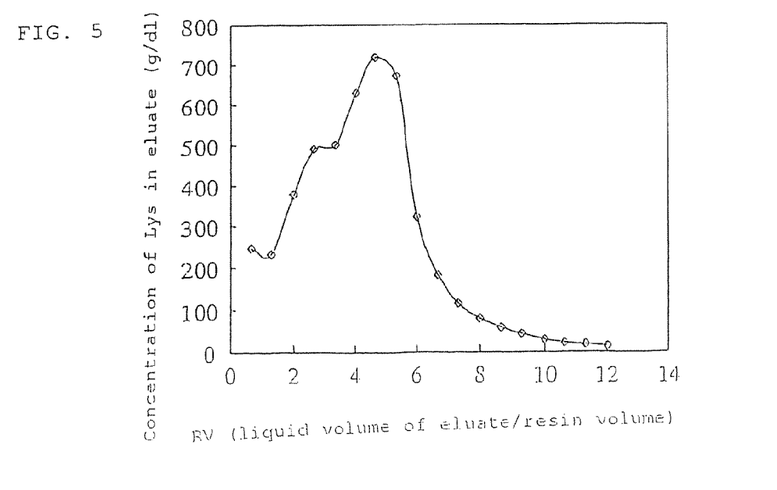
FIG. 5 shows an elution curve of a basic amino acid from a carbonate-type anion exchange resin.

The elution curve of eluting glutamic acid (GH) from the resin with an eluent liquid is shown in FIG. 3, the elution curve of eluting phenylalanine (Phe) from the resin with an eluent liquid is shown in FIG. 4, and the elution curve of eluting lysine (Lys) from the resin with an eluent liquid is shown in FIG. 5, respectively. In each elution curve, the liquid volume of eluate per the resin volume (RV) has a maximum value and the tailing is relatively small. Therefore, a phenomenon that the amino acid adsorbed on the resin remains adsorbed indefinitely and does not eluted can be avoided, and hence this process is a sufficiently valuable process in practical.

Recovery of Eluent from Eluate

The thus obtained eluate contains a carbonate ion, a hydrogen carbonate ion, and an ammonium ion which are eluents, but the eluents can be vaporized and removed as shown in formulae (19) to (22) by releasing the eluate to normal pressure and, if necessary, conducting a heating and/or a concentration. They can be recycled and reused as eluents and fermentation materials. On the other hand, in the case of producing an amino acid or a salt thereof, the purity of the amino acid and the salt thereof is increased by carrying out these steps, and hence the case is preferable.

In the case that an eluate contains an aqueous carbonic acid solution $$\text{HCO}_3^- \rightarrow \text{OH}^- + \text{CO}_2\uparrow \quad (19)$$

$$\text{H}_2\text{O} + \text{CO}_3^{2-} \rightarrow 2\text{OH}^- + \text{CO}_2\uparrow \quad (20)$$

In the case that an eluate contains an aqueous ammonium carbonate solution $$\text{NH}_4\text{HCO}_3 \rightarrow \text{NH}_3\uparrow + \text{CO}_2\uparrow + \text{H}_2\text{O} \quad (21)$$

$$(\text{NH}_4)_2\text{CO}_3 \rightarrow 2\text{NH}_3\uparrow + \text{CO}_2\uparrow + \text{H}_2\text{O} \quad (22)$$

Production of Sodium Glutamate Salt

In the case that the amino acid is especially glutamic acid, since ammonium glutamate (GluNH$_4$) is present in the eluate, by adding sodium hydroxide to the liquid from which excessive eluent is removed, the following reaction occurs and sodium glutamate (GluNa) can be obtained.

$$\text{GluNH}_4 + \text{NaOH} \rightarrow \text{GlueNa} + \text{NH}_3\uparrow + \text{H}_2\text{O} \quad (23)$$

Since the reaction of the formula (23) proceeds extremely smoothly, it is sufficient that sodium hydroxide to be added may be in an amount equimolar to the glutamic acid. As a result, a sodium glutamate solution having a high purity can be obtained in the eluate. In this case, when potassium hydroxide is used instead of sodium hydroxide, a potassium salt is obtained. In the case that the amino acid is aspartic acid, sodium aspartate or potassium aspartate is obtained by a similar treatment with an aqueous alkali solution.

Figure 1:
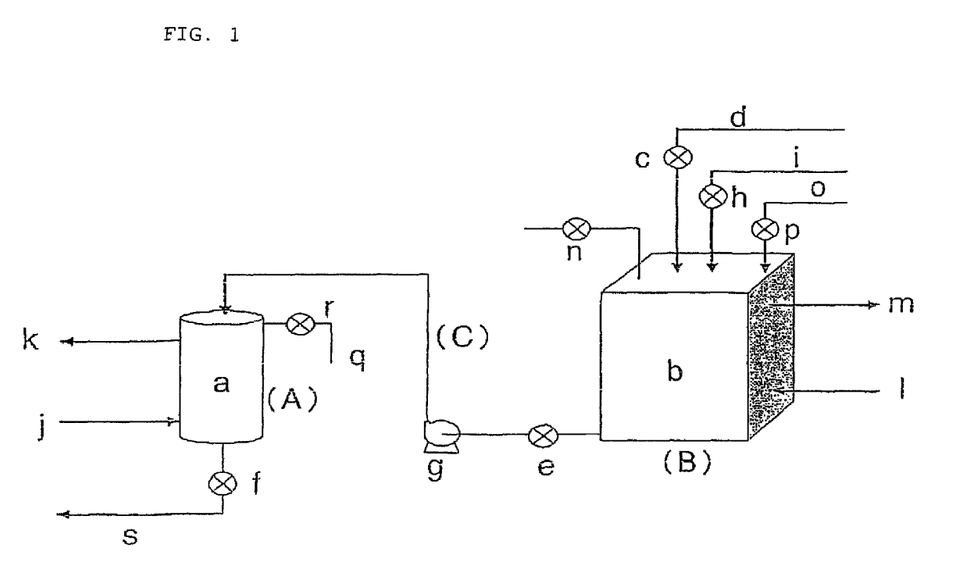
FIG. 1 shows a production apparatus of an amino acid or a salt thereof by the anion exchange resin process of the present invention.

Furthermore, the production of an acidic amino acid is exemplified in detail with reference to Drawings. The acidic amino acid-containing aqueous solution obtained by removing fermentation bacteria body from an L-glutamic acid fermentation liquid is controlled to around neutral pH and then stored in a reservoir tank b. Compressed air is fed from an air line d to pressurize the inner pressure of the reservoir tank b to about 0.2 to 1 MPa. At this moment, a pressure tight column a and the reservoir tank b are preferably kept at a constant temperature by circulating water having a temperature of 20° C. in a jacket through cooling water lines l, m, j, and k. Then, by working a pump g, transfer of the L-glutamic acid fermentation liquid to the pressure tight column is started. Air bubbles accumulated at the top of the column is sufficiently removed and the inside of the pressure tight column a is filled with the liquid. In order to adsorb the amino acid on the anion exchange resin, a valve f is opened and the liquid is started to drain and the ion exchange reaction is initiated. At this moment, the graduations of the pump and the opening degree of a pressure-reducing valve are controlled so that the inner pressure of the pressure tight column is made higher than normal pressure, i.e., from 0.1 to 1 MPa and a flow rate of the liquid transfer is from 0.1 to 2 L/hr. The time for the liquid transfer varies depending on the volume of the pressure tight column. The acidic amino acid is adsorbed on the carbonate-type anion exchange resin. During the adsorption reaction, no bubble formation of carbon dioxide gas in the pressure tight column occurs.

Washing Step

After the pressure of the reservoir tank b is released, the liquid in the reservoir tank b is discharged to emptiness and then pure water is fed to the reservoir tank from a feed inlet o. After the inner pressure is adjusted to 0.1 to 2 MPa with air, the remaining acidic amino acid-containing aqueous solution in the pressure tight column a is washed out.

Elution Step

An aqueous ammonium solution having a pH of 10 to 13 is placed in the reservoir tank b. Carbon dioxide gas is also injected thereinto to prepare an aqueous ammonium carbonate solution. Cold water is circulated in jackets of the pressure tight column a and the reservoir tank b to keep the temperature constant, and the aqueous ammonium carbonate solution is transferred to the pressure tight column a. It is preferable that the inner pressure of the pressure tight column a is from 0.1 to 2 MPa and the flow rate of the liquid transfer is from 0.1 to 1 L/hr. Thus, an acidic amino acid eluted from the anion exchange resin can be obtained.

After the acidic amino acid-containing eluate is concentrated by heating under vacuum, the liquid is neutralized by adding an aqueous sodium hydroxide solution so that the amount of the sodium hydroxide is equimolar to L-glutamic acid in the liquid. If necessary, the liquid is concentrated by heating under vacuum, and then an acidic amino acid salt can be obtained.

Production of Neutral Amino Acid

The production of a neutral amino acid and the constitution of the production apparatus can be performed in accordance with the method described in the production method of the acidic amino acid. The following will describe the different points. In order to achieve the adsorption on the anion exchange resin, it is possible to control a neutral amino acid-containing aqueous solution to pH 8 to 13, preferably pH 10 to pH 11, to thereby charge the ammonium ion co-existing in the fermentation liquid negatively and facilitate the adsorption of the neutral amino acid on the anion exchange resin. As the eluent liquid, an aqueous carbonic acid solution, an aqueous hydrogen carbonate solution, an aqueous ammonium carbonate solution, or an aqueous ammonium hydrogen carbonate solution can be used. As the apparatus for the purification and the production of the neutral amino acid, the aforementioned apparatus as shown in FIG. 1 can be used as it is. In the case of the neutral amino acid, since it is neutral in an eluate, no salt is formed.

Production of Lysine Hydrochloride

In the case that the amino acid is lysine, as the eluent liquid, an aqueous ammonium carbonate solution or an aqueous ammonium hydrogen carbonate solution is used. In this case, since lysine is present in an ionized form (Lys+) in the eluent liquid, the following reaction occurs and lysine hydrochloride (LysHCl) is obtained by adding hydrochloric acid to the liquid from which excessive eluent is removed.

$$Lys{++}HCl \rightarrow LysHCl \quad (24)$$

Since the reaction of the formula (24) extremely smoothly proceeds, it is sufficient that the hydrochloric acid to be added may be in an amount equimolar to the lysine. As a result, an aqueous lysine hydrochloride solution having a high purity can be obtained in the eluate.

Recovery of Eluent from Breakthrough Liquid

The following will describe a step of recovering an eluent and effective components from a breakthrough liquid. In the breakthrough liquid discharged from the adsorption step, carbonate ion and hydrogen carbonate ion released from the anion exchange resin and an ammonium component used for controlling the hydrogen ion concentration in pH control, fermentation, and purification before the treatment with the ion exchange resin are present. Upon release to normal pressure, the carbonate ion is converted into a gas to form bubbles and the ammonium component also vaporizes, so that these components almost disappear in the breakthrough liquid. Furthermore, when the liquid is heated to about 70° C. and simultaneously concentrated, the carbonate ion and the hydrogen carbonate ion and also simultaneously the ammonium ion can be further removed from the liquid since the solubility of carbon dioxide gas derived from the carbonate ion decreases as the temperature elevates. As a result, since the eluent and the ammonium ion in the breakthrough liquid can be reduced to almost nil, the amount of by-products can be diminished to a large extent. As above, when the carbon dioxide gas and the ammonia gas are co-existed at the same time, it is possible to utilize them in their entirety without separation. On the other hand, it is necessary to separate these components from each other for recycling these components as eluents according to the purposes, or as a pH controller, nitrogen source, or the like at the time of fermentation. For the separation, the ammonia gas component can be distilled and separated by the method disclosed in JP-A-55-139815, for example. As a result, since the vaporized carbon dioxide gas can be recovered and recycled as an eluent and the vaporized ammonia can be recovered and recycled in the fermentation and purification before the treatment with the ion exchange resin, their recovery results in the effective utilization and the recycle of the resources or the reduction of production cost.

Recovery of Eluent from Eluate

The following will describe a step of recovering an eluent from an eluate. As the eluent liquid, an aqueous ammonium carbonate solution or an aqueous ammonium hydrogen carbonate solution is used for an acidic amino acid, an aqueous carbonic acid solution, an aqueous hydrogen carbonate solution, an aqueous ammonium carbonate solution, or an aqueous ammonium hydrogen carbonate solution is used for a neutral amino acid, and an aqueous ammonium carbonate solution or an aqueous ammonium hydrogen carbonate solution is used for a basic amino acid. The amino acid adsorbed on the anion exchange resin is eluted from the anion exchange resin with the eluent liquid, and simultaneously the anion exchange resin is converted into the carbonate-type by adsorbing carbonate ion or hydrogen carbonate ion present in the eluent liquid, whereby the anion exchange resin is regenerated. Part of unexchanged carbonate ion and ammonium ion are not adsorbed on the anion exchange resin and directly passed through the anion exchange resin column. Therefore, carbonate ion, hydrogen carbonate ion, and ammonium ion are present as the eluent components in the eluate, and hence they can be recovered and recycled in the present invention. After the adsorption step, when the pressure tight column is left open to normal pressure by returning the pressure of the pressure tight column packed with the anion exchange resin to normal pressure, carbonate ion is converted into a gas to form bubbles and the ammonium component also vaporizes, so that these components almost disappear in the eluate. Furthermore, when the liquid is heated to about 70° C. and simultaneously concentrated, carbonate ion and hydrogen carbonate ion and also simultaneously ammonium ion can be further removed from the liquid, since the solubility of carbon dioxide gas decreases as the temperature elevates. As a result, since the eluent and the ammonium ion in the breakthrough liquid can be reduced to almost nil, the amount of by-products can be diminished to a large extent. As mentioned above, these separated eluents can be further separated according to the purposes and recycled, if necessary.

Production Apparatus of Amino Acid or Salt Thereof

The constitution of the production apparatus of an amino acid or a salt thereof of the present invention will be described with reference to FIG. 1. A pressure tight column a packed with an anion exchange resin for adsorbing the amino acid, a reservoir tank b for feeding an amino acid-containing aqueous solution thereto, and a pump g for transferring a fermentation liquid and an eluate from the reservoir tank b are provided and they are connected with a pipe line. Furthermore, the pressure tight column a possesses a drainage line s for draining a breakthrough liquid, eluate or washing liquid, a pressure-controlling valve f in the vicinity of outlet of the pressure tight column a disposed on the lines, a line q for gas drainage and a valve r for control thereof at the upper portion of the pressure tight column a, and circulating cooling water lines k and j. The reservoir tank b is constituted by a feed inlet o for feeding the fermentation liquid, aqueous ammonium solution or eluate, an air line d for pressurization, a line i for feeding an eluent, valves c, h, n, and p for controlling the feed of substances from these lines, a valve e for controlling pressure in the reservoir tank and discharging amount existing at outlet of the reservoir tank, and cooling water lines l and m.

EXAMPLES

The following will describe the present invention specifically with reference to Examples. Each measurement was carried out according to the following method.

L-Phenylalanine Concentration, L-Glutamic Acid Concentration, L-Proline Concentration, and L-Lysine Concentration These concentrations were measured by a Hitachi high-speed amino acid analyzer model L-8500 manufactured by Hitachi, ltd.

Carbonate Ion Concentration

The concentration was measured by a laboratory TOC-TN measuring apparatus model TNC-6000 manufactured by Toray Engineering Co., Ltd. The inorganic substance carbon concentration obtained by the analysis was regarded as a carbonate concentration.

Ammonium Ion Concentration

The concentration was measured by a distillation method using a keltech autosampler system model 1035/38 manufactured by Japan General K.K.

Sodium Ion Concentration

The concentration was measured by a polarizing Zeeman atomic absorption spectrophotometer model Z-8100 manufactured by Hitachi, ltd.

Calculation of Ammonium Ion Quantity $W_{NH4}$ (%) in Breakthrough Liquid $$W_{NH4}\ (\%) = CV \cdot CV_{NH4} \cdot 100 / RV / RV_{NH4} \tag{25}$$

(wherein CV: concentrated breakthrough liquid volume (L), $CV_{NH4}$: ammonium ion quantity (g/L) in concentrated breakthrough liquid, RV: breakthrough liquid volume (L), $RV_{NH4}$: ammonium ion quantity (g/L) in breakthrough liquid)

Calculation of Possible Recovering Quantity of Ammonium Ion $R_{NH4}$ (%) from Breakthrough Liquid $$R_{NH4}\ (\%) = 100 - W_{NH4} \tag{26}$$

Calculation of Carbonate Ion Quantity $W_{CO3}$ (%) in Breakthrough Liquid $$W_{CO3}\ (\%) = CV \cdot CV_{CO3} \cdot 100 / RV / RV_{CO3} \tag{27}$$

(wherein CV: concentrated breakthrough liquid volume (L), $CV_{CO3}$: carbonate ion quantity (g/L) in concentrated breakthrough liquid, RV: breakthrough liquid volume (L), $RV_{CO3}$: carbonate ion quantity (g/L) in breakthrough liquid)

Calculation of Possible Recovering Quantity of Carbonate Ion $R_{CO3}$ (%) from Breakthrough Liquid $$R_{CO3}\ (\%) = 100 - W_{CO3} \tag{28}$$

Example 1

Purification of L-Glutamic Acid Fermentation Liquid

Preparation of Carbonate-Type Anion Exchange Resin

A strongly basic anion exchange resin SA-10A manufactured by Mitsubishi Chemical Corporation was used as an anion exchange resin. First, 4 L of a 0.75 mol/L aqueous sodium hydrogen carbonate solution was passed through 0.4 L of the chlorine-type anion exchange resin at 1 L/h for 4 hours to convert the ion exchange resin into a carbonate-type. The resin was thoroughly washed with pure water.

Adsorption Step

The whole amount (0.4 L) was packed in the pressure tight column a in FIG. 1. FIG. 1 is referred to in the following explanation. Into the reservoir tank b in FIG. 1 was introduced, from the liquid feed inlet o, an L-glutamic acid-containing aqueous solution (bacteria body-treated fermentation liquid) of pH 7 having an L-glutamic acid content of 122 g/L, from which fermented bacteria body had been removed using a microfiltration membrane, followed by closure of the valve p. Then, after the closure of the valves h and n was confirmed, the valve c was opened and compressed air was fed from the air line d to pressurize the inner pressure of the reservoir tank to 0.4 MPa. At this moment, the pressure tight column and the reservoir tank were kept at a constant temperature by circulating water having a temperature of 20° C. in jackets through the cooling water lines j, k, l, and m. Then, the valves e and r were opened and further, by working the pump g, transfer of the L-glutamic acid fermentation liquid to the pressure tight column was started. For an initial few minutes, air bubbles accumulated at the top of the column was sufficiently removed from the upper portion of the column through the valve r using the liquid drainage line q to fill the inside of the pressure tight column with the liquid. Thereafter, by closing the valve r and opening the valve f, the liquid was started to drain from the bottom of the column and the ion exchange reaction was initiated. At this moment, the graduations of the pump and the opening degree of the pressure-reducing valve were controlled so as to be an inner pressure of the pressure tight column of 0.5 MPa and a flow rate of the liquid transfer of 0.6 L/hr. The liquid transfer was continued for 4 hours and L-glutamic acid was adsorbed on the carbonate-type anion exchange resin. During the adsorption reaction, no bubble formation of carbon dioxide gas in the pressure tight column occurred and a satisfactory adsorption was achieved. Thereby, a breakthrough liquid of 2.4 L/hr was obtained.

Washing Step

Then, the pump g was stopped and the pressure-reducing valve f and the valve e were closed. After the pressure of the reservoir tank b was released by closing the valve c and opening the pressure-releasing valve n, the valve p was opened and pure water was fed to the reservoir tank from the liquid feed inlet o. After an inner pressure of 0.4 MPa was applied to the reservoir tank by closing the valves p and n, opening the valve c, and feeding air from the air line d, feed of pure water was started by opening the valve e and the pressure-reducing valve f and further working the pump g in FIG. 1. At this moment, the graduations of the pump and the opening degree of the pressure-reducing valve were controlled so as to be an inner pressure of the pressure tight column of 0.5 MPa and a flow rate of the liquid transfer of 0.8 L/hr. The liquid transfer was continued for 4 hours and the L-glutamic acid fermentation liquid remained in the anion exchange resin layer was washed out.

Elution Step

Then, the pump g was stopped and the pressure-reducing valve f and the valve e were closed. After the pressure of the reservoir tank b was released by closing the valve c and opening the pressure-releasing valve n, the valve p was opened and an aqueous ammonium solution having a hydrogen ion concentration of 11 was fed to the reservoir tank from the liquid feed inlet o. Then, the valves p and n were closed and the valve h was opened. Thereby, feed of carbon dioxide gas was started from the carbon dioxide gas line l to initiate the dissolution of carbon dioxide gas into an aqueous ammonium solution. At this moment, cold water having a temperature of 5° C. was circulated in jackets of the pressure tight column and the reservoir tank to keep the temperature constant. After the inner pressure of the reservoir tank was kept constant at 0.6 MPa, transfer of the aqueous ammonium carbonate solution was started by opening the valve e and the pressure-reducing valve f and further working the pump g. At this moment, the graduations of the pump and the opening degree of the pressure-reducing valve were controlled so as to be an inner pressure of the pressure tight column of 0.7 MPa and a flow rate of the liquid transfer of 0.7 L/hr. The liquid transfer was continued for 2 hours and L-glutamic acid was eluted from the anion exchange resin to obtain 1.4 L of an eluate. The concentration of L-glutamic acid at this moment was 15.7 g/L.

Deaerating Step

The eluate was transferred to a deaerating apparatus da and the dissolved carbon dioxide and ammonia were separated through vaporization by concentrating the eluate under reduced pressure to a volume of 0.62 L. In the resulting concentrated eluate, the concentration of L-glutamic acid was 35.8 g/L and the concentration of ammonia was 1.9 g/L. The remaining ammonium ion was present as a counter ion of L-glutamic acid. The separated carbon dioxide gas and ammonia were transferred to a separation-recovery apparatus sp and recovered. The carbon dioxide gas can be recycled as an eluent, and the ammonia as a fermentation starting material, a pH controlling liquid, or an eluent.

Example 2

Purification of L-Phenylalanine Fermentation Liquid

Adsorption Step

An adsorption operation of L-phenylalanine onto the anion exchange resin prepared by preparation of carbonate-type anion exchange resin in Example 1 was carried out in accordance with the procedure in Example 1. At that time, as a fermentation liquid, a liquid obtained by removing bacteria body with a microfiltration membrane and converting the ionic form of L-phenylalanine into an anion form by controlling the pH to 10 using an aqueous ammonium solution was used. The concentration of L-phenylalanine was 29.7 g/L. The feed flow rate to the pressure tight column was 0.6 L/hr and the liquid-transferring time was 2.67 hours. Moreover, the pressure of the reservoir tank was 0.4 MPa, the pressure of the pressure tight column was 0.5 MPa, and the temperature was 20° C. During the adsorption reaction, no bubble formation of carbon dioxide gas occurred. Thereby, a breakthrough liquid of 1.6 L/hr was obtained.

Washing Step

Then, the resin was washed in the same manner as in Example 1. Pure water was used as a washing water and the flow rate was 0.8 L/hr, the liquid-transferring time was 4 hours, the pressure of the reservoir tank was 0.4 MPa, the pressure of the pressure tight column was 0.5 MPa, and the temperature was 20° C.

Elution Step

Then, elution of L-phenylalanine from the anion exchange resin was carried out. The operation procedure was the same as in Example 1 but pure water in which carbon dioxide gas was dissolved was used instead of the aqueous ammonium solution. The flow rate was 1.6 L/hr, the liquid-transferring time was 2.25 hours, the pressure of the reservoir tank was 0.5 MPa, the pressure of the pressure tight column was 0.6 MPa, and the temperature was 25° C. L-phenylalanine was eluted from the anion exchange resin to obtain 3.6 L of an eluate. The concentration of L-phenylalanine at this moment was 7.0 g/L.

Deaerating Step

The eluate was transferred to a deaerating apparatus da and the dissolved carbon dioxide and ammonia were separated as gases by reducing the pressure into a volume of 1.8 L. In the resulting concentrated eluate, the concentration of L-phenylalanine was 14.1 g/L. The separated carbon dioxide gas and ammonia were transferred to a separation-recovery apparatus sp and recovered. The carbon dioxide gas can be recycled as an eluent, and the ammonia as a fermentation starting material, a pH controlling liquid, or an eluent.

Example 3

Purification of L-Proline

Adsorption Step

An adsorption operation of L-proline onto the anion exchange resin prepared by preparation of carbonate-type anion exchange resin in Example 1 was carried out in accordance with the procedure in Example 1. A liquid obtained by converting the ionic form of L-proline into an anion form by controlling the pH to 10 using an aqueous ammonium solution was used. The concentration of L-proline was 106 g/L. The feed flow rate to the pressure tight column was 0.6 L/hr and the liquid-transferring time was 2.67 hours. Moreover, the pressure of the reservoir tank was 0.4 MPa, the pressure of the pressure tight column was 0.5 MPa, and the temperature was 20° C. During the adsorption reaction, no bubble formation of carbon dioxide gas occurred. Thereby, a breakthrough liquid of 1.6 L/hr was obtained.

Washing Step

Then, the resin was washed in the same manner as in Example 1. Pure water was used as a washing water and the flow rate was 0.8 L/hr, the liquid-transferring time was 4 hours, the pressure of the reservoir tank was 0.4 MPa, the pressure of the pressure tight column was 0.5 MPa, and the temperature was 20° C.

Elution Step

Then, elution of L-proline from the anion exchange resin was carried out. The operation procedure was the same as in Example 2 and pure water in which carbon dioxide gas was dissolved was used. The flow rate was 1.6 L/hr, the liquid-transferring time was 3.0 hours, the pressure of the reservoir tank was 0.5 MPa, the pressure of the pressure tight column was 0.6 MPa, and the temperature was 25° C. L-proline was eluted from the anion exchange resin to obtain 4.8 L of an eluate. The concentration of L-proline at this moment was 8.0 g/L.

Deaerating Step

The eluate was transferred to a deaerating apparatus da and the dissolved carbon dioxide and ammonia were separated as gases by concentration under reduced pressure into a volume of 2.4 L. In the resulting concentrated eluate, the concentration of L-proline was 38.3 g/L. The separated carbon dioxide gas and ammonia were transferred to a separation-recovery apparatus sp and recovered. The carbon dioxide gas can be recycled as an eluent, and the ammonia as a fermentation starting material, a pH controlling liquid, or an eluent.

Example 4

Purification of L-Lysine

Adsorption Step

This Example shows an example wherein the invention is applied to an aqueous solution containing L-lysine, which is one of basic amino acids. An adsorption operation of L-lysine onto the anion exchange resin prepared by preparation of carbonate-type anion exchange resin in Example 1 was carried out in accordance with the procedure in Example 1. A liquid obtained by converting the ionic form of L-lysine into an anion form by controlling the pH to 12 using an aqueous ammonium solution was employed. The concentration of L-lysine was 16.7 g/L. The feed flow rate to the pressure tight column was 0.6 L/hr and the liquid-transferring time was 3.0 hours. Moreover, the pressure of the reservoir tank was 0.4 MPa, the pressure of the pressure tight column was 0.5 MPa, and the temperature was 20° C. During the adsorption reaction, no bubble formation of carbon dioxide gas occurred. Thereby, a breakthrough liquid of 1.8 L/hr was obtained.

Washing Step

Then, the resin was washed in the same manner as in Example 1. Pure water was used as a washing water and the flow rate was 0.8 L/hr, the liquid-transferring time was 4 hours, the pressure of the reservoir tank was 0.4 MPa, the pressure of the pressure tight column was 0.5 MPa, and the temperature was 20° C.

Elution Step

Elution of L-lysine from the anion exchange resin was carried out. The operation procedure was the same as in Example 1 and an aqueous ammonium solution having a hydrogen ion concentration of 11 in which carbon dioxide gas was dissolved was used. The flow rate was 1.6 L/hr, the liquid-transferring time was 3.0 hours, the pressure of the reservoir tank was 0.5 MPa, the pressure of the pressure tight column was 0.6 MPa, and the temperature was 25° C. L-lysine was eluted from the anion exchange resin to obtain 4.8 L of an eluate. The concentration of L-lysine at this moment was 3.1 g/L.

Deaerating Step

The eluate was transferred to a deaerating apparatus da and the dissolved carbon dioxide and ammonia were separated as gases by concentration under reduced pressure into a volume of 1.1 L. In the resulting concentrated eluate, the concentration of L-lysine was 14.4 g/L, and the concentration of carbonate ion was 1.4 g/L. The remaining carbon dioxide is present as a carbonate ion, and served as the counter ion of L-lysine. The separated carbon dioxide gas and ammonia were transferred to a separation-recovery apparatus sp and recovered. The carbon dioxide gas can be recycled as an eluent, and the ammonia as a fermentation starting material, a pH controlling liquid, or an eluent.

Example 5

Production of Sodium L-Glutamate

To 0.62 L of the concentrated eluate (concentration of L-glutamic acid: 35.8 g/L, concentration of ammonium ion: 7.9 g/L) obtained in Example 1 was added an aqueous sodium hydroxide solution so that the amount of sodium hydroxide became equimolar to L-glutamic acid in the liquid, whereby neutralization was achieved. As a result, the volume of the eluate became 0.99 L. By concentrating the liquid under heating at 86° C. under vacuum until the volume was decreased to 0.30 L, ammonia was separated as a gas and an aqueous sodium L-glutamate solution having a composition of concentration of L-glutamic acid: 73.0 g/L, concentration of carbonate ion: not detected, concentration of ammonium ion: not detected, and sodium: 5.6 g/L was obtained. The separated ammonia gas was transferred to a separation-recovery apparatus sp and recovered.

Example 6

Production of L-Lysine Hydrochloride

To 1.01 L of the concentrated eluate (concentration of L-lysine: 14.4 g/L, concentration of ammonium ion: 1.4 g/L) obtained in Example 4 was added hydrochloric acid so that the amount of hydrochloric acid became equimolar to L-lysine in the liquid, whereby neutralization was achieved. As a result, the volume of the eluate became 1.11 L. By concentrating the liquid under heating at 86° C. under vacuum until the volume was decreased to 0.30 L, carbon dioxide gas was separated and an aqueous L-lysine solution having a composition of concentration of L-lysine: 73.0 g/L, concentration of carbonate ion: not detected, concentration of ammonium ion: not detected, and concentration of chlorine ion: 5.6 g/L was obtained. The separated carbon dioxide gas was transferred to a separation-recovery apparatus sp and recovered.

Example 7

Figure 2:
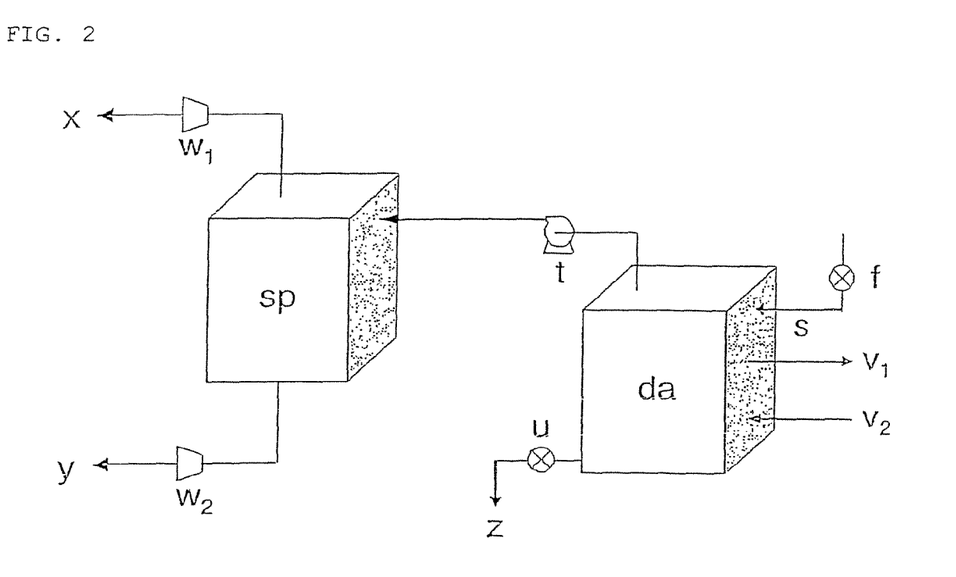
FIG. 2 shows a recovering apparatus of an eluent component or an ammonium component as a pH controlling or nitrogen source, which are present in an eluate or a breakthrough liquid of the present invention.

Recovery and Separation of Carbon Dioxide Gas and Ammonia from Breakthrough Liquid and Eluate of L-Glutamic Acid Of the breakthrough liquids obtained in the adsorption step in Example 1, 0.4 L of the breakthrough liquid (concentration of carbonate ion: 85.4 g/L, concentration of ammonium ion: 12.6 g/L) obtained until 0.67 hours had passed after the start of the adsorption was transferred to a deaerating apparatus da in FIG. 2 and concentrated under heating at a temperature of 80° C. under vacuum to obtain 0.08 L of a concentrated liquid and 0.32 L of a mixed gas. In the concentrated breakthrough liquid, the concentration of carbonate ion was 1.0 g/L and the concentration of ammonium ion was 8.5 g/L. The mixed gas was transferred to a separation apparatus sp and 4.4 g of ammonia and 24.6 g of carbon dioxide gas were separated and recovered. The amount of ammonium ion $W_{NH4}$ (%) in the breakthrough liquid was 13.5% based on the formula (24). The amount of carbonate ion $W_{CO3}$ (%) in the breakthrough liquid was 0.2% based on the formula (24). Therefore, 86.5% of ammonium ion was recovered from the breakthrough liquid based on the formula (23). On the other hand, based on the formula (25), 99.8% of carbonate ion eluted from the anion exchange resin could be recovered. Similarly, with regard to the eluate, by the deaerating step described in Example 1 and the production step of L-glutamic acid described in Example 5, ammonium ion and carbonate ion could be recovered in 99.8% and 99.0%, respectively. Not only the removal of the impurities from the breakthrough liquid, which is a waste water, by the present invention was preferable as an environmental measure but also the impurities diminished were recycled as eluents and fermentation additives.

Example 8

Recovery and Separation of Carbon Dioxide Gas and Ammonia from Breakthrough Liquid and Eluate of L-Proline Of the breakthrough liquids obtained in the adsorption step in Example 3, 0.4 L of the breakthrough liquid (concentration of carbonate ion: 85.4 g/L, concentration of ammonium ion: 6.7 g/L) obtained until 0.67 hours had passed after the start of the adsorption was transferred to a deaerating apparatus da in FIG. 2 and concentrated under heating at a temperature of 80° C. under vacuum to obtain 0.09 L of a concentrated liquid and 0.31 L of a mixed gas. In the concentrated breakthrough liquid, the concentration of carbonate ion was 1.5 g/L and the concentration of ammonium ion was 1.2 g/L. The mixed gas was transferred to a separation apparatus sp and 2.6 g of ammonia and 24.5 g of carbon dioxide gas were separated and recovered. The amount of ammonium ion $W_{NH4}$ (%) in the breakthrough liquid was 4.0% based on the formula (24). The amount of carbonate ion $W_{CO3}$ (%) in the breakthrough liquid was 0.4% based on the formula (24). Therefore, 96.0% of ammonium ion was recovered from the breakthrough liquid based on the formula (23). On the other hand, based on the formula (25), 99.6% of carbonate ion eluted from the anion exchange resin could be recovered. Similarly, with regard to the eluate, by the deaerating step described in Example 3, carbonate ion could be recovered in 99.9%. Not only the removal of the impurities from the breakthrough liquid, which is a waste water, by the present invention was preferable as an environmental measure but also the impurities diminished were recycled as eluents and fermentation additives.

Example 9

Recovery and Separation of Carbon Dioxide Gas and Ammonia from Breakthrough Liquid of L-Lysine Of the breakthrough liquids obtained in the adsorption step in Example 4, 0.8 L of the breakthrough liquid (concentration of carbonate ion: 42.7 g/L, concentration of ammonium ion: 167 g/L) obtained until 1.33 hours had passed after the start of the adsorption was transferred to a deaerating apparatus da in FIG. 2 and concentrated under heating at a temperature of 80° C. under vacuum to obtain 0.16 L of a concentrated liquid and 0.64 L of a mixed gas. In the concentrated breakthrough liquid, the concentration of carbonate ion was 6.0 g/L and the concentration of ammonium ion was 1.9 g/L. The mixed gas was transferred to a separation apparatus sp and 133.3 g of ammonia and 23.9 g of carbon dioxide gas were separated and recovered. The amount of ammonium ion $W_{NH4}$ (%) in the breakthrough liquid was 0.2% based on the formula (24). The amount of carbonate ion $W_{CO3}$ (%) in the breakthrough liquid was 2.8% based on the formula (24). Therefore, 99.8% of ammonium ion was recovered from the breakthrough liquid based on the formula (23). On the other hand, based on the formula (25), 97.2% of carbonate ion eluted from the anion exchange resin could be recovered. Similarly, with regard to the eluate, by the deaerating step described in Example 4 and the production step of L-glutamic acid described in Example 5, ammonium ion and carbonate ion could be recovered in 99.8% and 99.2%, respectively. Not only the removal of the impurities from the breakthrough liquid, which is a waste water, by the present invention was preferable as an environmental measure but also the impurities diminished were recycled as eluents and fermentation additives.

INDUSTRIAL APPLICABILITY

The invention relates to a process for producing an amino acid or an amino acid salt from an amino acid-containing aqueous solution using a carbonate-type anion exchange resin, and a system of reducing the amount of by-products generated from an adsorption step and recovering an eluent from a breakthrough liquid and/or an eluate for recycling.

The invention claimed is:

1. A method for recovering an eluent, which comprises heating or optionally heating under reduced pressure, a breakthrough liquid which is discharged from a pressure tight column through an adsorption step of adsorbing a free amino acid contained in an amino acid-containing aqueous solution on the pressure tight column while the solution passes through the pressure tight column packed with a carbonate-type anion exchange column under elevated pressure, and/or an eluate which is discharged from the pressure tight column through an elution step comprising injecting an eluent liquid containing a hydrogen carbonate ion and/or carbonate ion under pressure into the pressure tight column under elevated pressure, eluting the amino acid adsorbed on the anion exchange resin, and simultaneously regenerating the anion exchange resin into the carbonate-type and from which the amino acid or a salt thereof is removed, to vaporize a carbonate ion, and acidic carbonate ion, or an ammonium ion to thereby recover the eluent as a carbon dioxide gas or an ammonia gas.

* * * * *